United States Patent [19]
Jakus

[11] Patent Number: 5,557,801
[45] Date of Patent: Sep. 24, 1996

[54] DEVICE FOR RETAINING BODY HEAT

[76] Inventor: Stephen A. Jakus, 85 Lux St., Rochester, N.Y. 14621

[21] Appl. No.: 412,767

[22] Filed: Mar. 29, 1995

[51] Int. Cl.⁶ .................................................. A41D 13/00
[52] U.S. Cl. .............................. 2/2; 2/69; 2/48; 607/108
[58] Field of Search ................................... 2/69, 92, 227, 2/338, 272, 211, 48, 51, 267, 22, 2; 607/108, 112, 114; 128/846

[56] References Cited

U.S. PATENT DOCUMENTS

| | | | |
|---|---|---|---|
| 1,445,274 | 2/1923 | Greenberg | 2/338 |
| 2,590,212 | 3/1952 | Samuels | 604/291 |
| 3,727,238 | 4/1973 | Wolfson | 2/69 |
| 4,459,703 | 7/1984 | Kosmas et al. | 2/338 |
| 4,603,441 | 8/1986 | Richter | 2/227 |
| 4,836,194 | 6/1989 | Sebastian et al. | 2/338 |
| 5,153,939 | 10/1992 | Howe et al. | 2/69 |
| 5,386,593 | 2/1995 | Kleinman | 2/338 |

FOREIGN PATENT DOCUMENTS

| | | | |
|---|---|---|---|
| 2047937 | 1/1993 | Canada | 2/69 |
| 6-081204 | 3/1994 | Japan | 2/338 |

*Primary Examiner*—Amy B. Vanatta
*Attorney, Agent, or Firm*—Howard J. Greenwald

[57] ABSTRACT

A body warmer containing a fabric shell and an interior chamber. The body warmer has a central body and two flaps joined to it; the flaps are adapted to be releasably connected to each other. The shell is preferably made from one piece of fabric which is folded and joined at its periphery. The central part of the shell has a top portion integrally joined to a bottom portion which decreases in length as the bottom of the shell is approached.

15 Claims, 1 Drawing Sheet

DEVICE FOR RETAINING BODY HEAT

FIELD OF THE INVENTION

A body warming article adapted to be worn around a person's waist.

BACKGROUND OF THE INVENTION

Devices for retaining a person's body heat, often referred to as "body warmers", are well known to those skilled in the art. Thus, by way of illustration, the prior art has disclosed disposable body warmers (see U.S. Pat. Nos. 5,366,492, 5,342,412, 5,046,479, and 4,925,743), body warmers for use under a blanket (see, e.g., U.S. Pat. No. 5,300,100), and a variety of other body warmers of various sizes, shapes, and utilities (see, e.g., U.S. Pat. Nos. 4,846,528, 4,841,646, 4,753,483, 4,282,005, and 4,241,721). The disclosure of each of the United States patents mentioned in this paragraph are hereby incorporated by reference into this specification.

To the best of applicant's knowledge and belief, however, the prior art has not provided a body warmer which is relatively inexpensive to make and use, which can be reused indefinitely, which does not require the addition of chemicals or the use of electricity for its function, and which is washable. It is an object of this invention to provide such a body warmer.

SUMMARY OF THE INVENTION

In accordance with this invention, there is provided an device for retaining body heat which is comprised of two flaps integrally connected to a central body portion. The flaps contain means for removably attaching one to the other. The central body portion is comprised of a cavity in which insulating, fibrous material is present.

BRIEF DESCRIPTION OF THE DRAWINGS

The present invention will be more fully understood by reference to the following detailed description thereof, when read in conjunction with the attached drawings, wherein like reference numerals refer to like elements, and wherein.

DESCRIPTION OF THE PREFERRED EMBODIMENTS

The body warmer of this invention is an insulated article of clothing that wraps around the body of a user. Thus, referring to FIG. 1, it will be seen that body warmer 10 is wrapped around the waist of user 12 with body portion 14 of body warmer 10 covering the kidneys (not shown) of the user 12.

Figure 1:
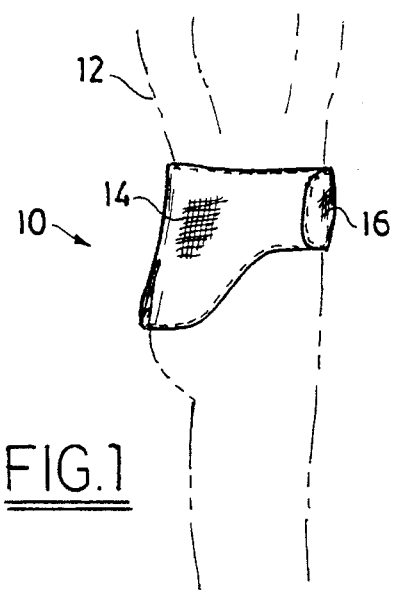
FIG. 1 is a perspective view of one preferred embodiment of the body warmer of this invention on the body of a user.

Although the body warmer 10 is shown in FIG. 1 contiguous with the skin of user 12, it will be apparent that such body warmer 10 can be worn on the outside of a user's clothes (not shown), or on the inside, like an undergarment.

Although applicant does not wish to be bound to any particular theory, he believes that his body warmer 10 functions effectively because it keeps a user's blood warm as it flows through the body. Approximately twenty-five percent of a person's blood flows through his kidneys ever minute. When the kidneys are kept warm, it is believed that the blood flowing through it also tends to keep warm.

Figure 2:
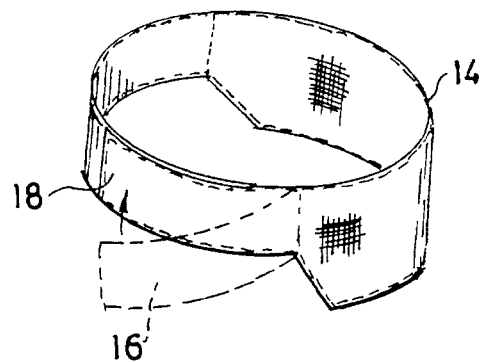
FIG. 2 is a perspective view of the body warmer of FIG. 1 showing its flaps connected to each other.
Figure 3:
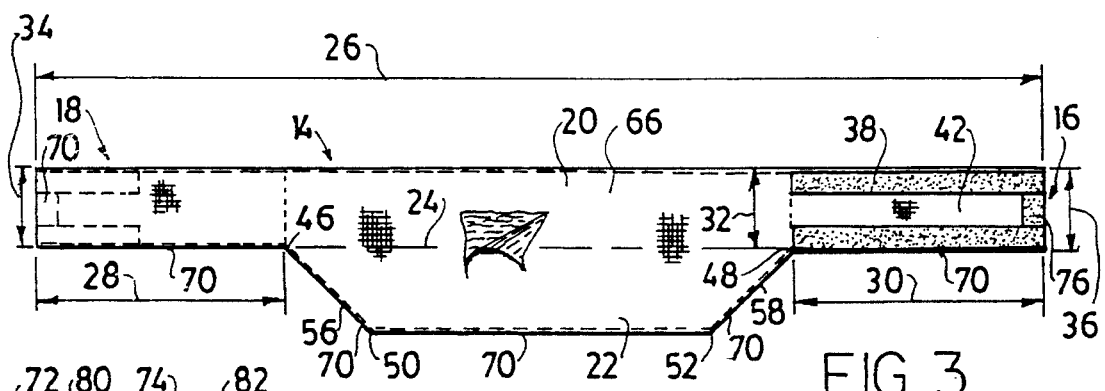
FIG. 3 is front view of the body warmer of FIG. 1.

Referring again to FIG. 1, it will be seen that flap 16 is removably attached to flap 18 (not shown in FIG. 1, but see FIGS. 2 and 3). The means for effecting such attachment will be discussed elsewhere in this specification.

Referring to FIGS. 1 and 3, it will be seen that the body portion 14 of body warmer 10 is comprised of an upper section 20 and a bottom section 22 which, for the sake of simplicity of representation, is shown separated by dotted line 24. It will be apparent to those skilled in the art that no such dotted line 24 actually appears in the device.

Referring to FIG. 1, it will be seen that the overall length 26 of body warmer 10 is from about 30 to about 60 inches and, preferably, is from about 39 to about 53 inches.

Referring again to FIG. 1, it will be seen that the lengths 28 and 30 of each of flaps 18 and 16, respectively, will preferably range from about 8 to about 16 inches and, preferably, will be from about 9 to about 13 inches. In one preferred embodiment, each of lengths 28 and 30, which may be the same or be different, will range from about 10 to about 13 inches and, most preferably, will be substantially equal to each other in length.

It is preferred that each of lengths 28 and 30 be at least about twenty-five percent of length 26.

Referring again to FIG. 2, it will be seen that the top portion 20 of body portion 14 preferably has a width which is from about 6 to about 8 inches. The widths 34 and 36 of flaps 18 and 16, respectively, preferably range from about 5 to about 8 inches and, generally, are from about 80 to about 100 percent of width 32 of upper portion 20 of body portion 14. It is more preferred, however, that widths 34 and 36 be from about 6 to about 8 inches and be at least about 90 percent of width 32.

Referring to FIGS. 2 and 3, it will be seen that each of flaps 28 and 30 is comprised of means for releasably fastening one such flap to the other. In the preferred embodiment illustrated in FIGS. 2 and 3, such releasable fastening means comprise "Velcro" separable loop material 38 (see FIG. 3), and Velcro separable hook material 40 (see FIG. 4). As will be apparent to those skilled in the art, when body warmer 10 is wrapped around the waist of a user 10 (see FIG. 1), loop material 38 contacts hook material 40 and releasably attaches the front side 42 of flap 16 (see FIG. 3) to the back side 44 of flap 18 (see FIG. 4).

Any conventional means for releasably attaching flap 16 to flap 18 may be used in the body warmer 10 of this invention. Thus, by way of illustration and not limitation, one may use one or more of the releasable attachment means disclosed in U.S. Pat. Nos. 5,369,852 (mixed hook/loop separable fasteners), 5,357,659 (snap fasteners), 5,328,400 (Velcro fabric fastener), 5,316,294 (hook/loop fastener), 5,287,571 (hook/loop fastener), 5,269,410 (hook/loop strip), 5,267,453, 5,247,182 (complementary fabric fastener means), 5,231,733 (hook/loop separable fasteners), 5,230,333 (snap fasteners), 5,193,549, 5,176,6780 (hook fastener made from polypropylene and loop fastener made from polyester), 5,157,799, 5,152,285, 4,959,265 (adhesive tape fastener), and the like. The disclosure of each of these United States patents is hereby incorporated by reference into this specification.

Referring again to FIGS. 3 and 4, the fastener materials 38 and 40 may be attached to flaps 16 and 18 by conventional means. Thus, by way of illustration and not limitation, they may be sewn onto the flaps 38 and 40, they may be attached by adhesive means, etc. Reference may be had to the aforementioned patents for various conventional means of attachment.

Referring again to FIGS. 3 and 4, it will be seen that the bottom section 22 of body portion 14 of body warmer 10 has a length which decreases from points 46 and 48 (at which points the length of bottom section 22 is substantially equal to the length of top section 20) to points 50 and 52 (at which point the minimum length 54 of bottom section 22 is less the length of the top section 20.

It is preferred that the length 56 of top section 20 (which is also equal to the maximum length of the bottom section 22) be such that the minimum length 54 of bottom section 22 is less than about 90 percent of length 56 and, more preferably, is from about 70 to about 90 percent of length 56. In one preferred embodiment, length 54 is from about 17 to about 21 inches and, more preferably, is from about 18 to about 20 inches; and length 56 is from about 23 to about 29 inches.

It will be apparent to those skilled in the art that, although the reduction of width between points 46 and 50, and 48 and 52, may be accomplished by straight walls (such as, e.g., walls 56 and 58), other shaped walls (such as curved walls) may also be used.

Figure 4:
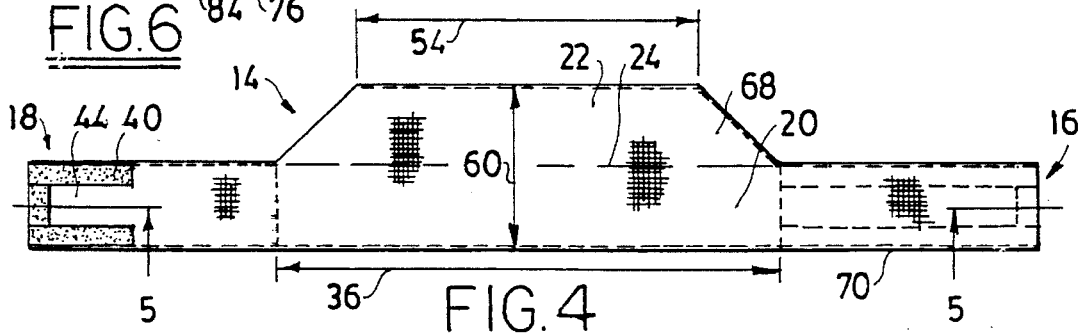
FIG. 4 is a back view of the body warmer of FIG. 1.

Referring to FIG. 4, it will be seen that the total width of body portion 14 will generally be from about 1.5 to about 2.5 times as great as width 32, and preferably will be from about 1.6 to about 2.0 times as great as width 32

In the embodiment depicted in FIGS. 1–4., the body warmer 10 is comprised of flaps 16 and 18 and body portions 20 and 22 which are made from a fabric material which, preferably, is comprised of cotton.

In one embodiment, the fabric material used is corduroy. As is known to those skilled in the art, corduroy is a cotton, rayon, or other fabric with a cut pile surface of wales; it may be either plain or twill weave. See, e.g., U.S. Pat. Nos. 4,870,727, 4,701,985, 4,180,606, 3,769,816, and the like. The disclosure of each of these United States patents is hereby incorporated by reference into this specification.

In another embodiment, the fabric material used is flannel. Flannel is a loosely woven, generally wool fabric with the wave concealed by a napped surface. See, e.g., U.S. Pat. Nos. 5,287,573, 5,244,625,. 4,916,782, 4,828,914, and the like. The disclosure of each of these United States patents is hereby incorporated by reference into this specification.

Other suitable fabric materials will be readily apparent to those skilled in the art. Thus, e.g., any of the fabric materials referred to in the aforementioned patents on body warmers also may be used.

In the preferred embodiment depicted in the Figures, body warmer 10 is made from two pieces of fabric material, front piece 66 (see FIG. 3), and back piece 68 (see FIG. 4) which are sewn or otherwise joined together at one or more points on either on the sides and/or bottom of such pieces. As will be apparent to those skilled in the art, the use of such a front and back piece will create a chamber between the front and back.

Figure 5:
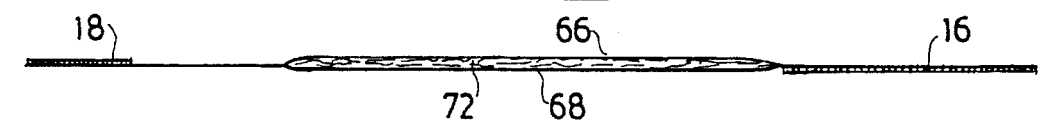
FIG. 5 is a side sectional view of the body warmer of FIG. 1.

One such chamber is illustrated in FIG. 5. Referring to FIG. 5, chamber 72 is defined between front section 66 of body portion 14, and back section 68 of body portion 14. In the embodiment illustrated, chamber 68 is filled (or substantially filled) with fibrous insulating material.

Any of the fibrous insulating materials known to those skilled in the art may be disposed within chamber 72. Thus, by way of illustration and not limitation, one may use one or more of the fibrous insulating materials disclosed in U.S. Pat. Nos. 5,335,310, 5,297,969, 5,287,674, 5,206,081 (cellulosic fibers), 4,769,194, 4,430,369, 4,360,440, 4,350,001, 3,921,273, and the like. The disclosure of each of these United States patents is hereby incorporated by reference into this specification.

In one preferred embodiment, the fibrous insulating material is fibrous polyester fiberfill such as, e.g., the fiberfill material disclosed in one or more of U.S. Pat. Nos. 5,064, 703, 4,869,771, 4,818,599, 4,794,038, 4,783,364, 4,618,531, 4,463,035, and the like. The disclosure of each of these U.S. patents is hereby incorporated by reference into this specification.

Figure 6:
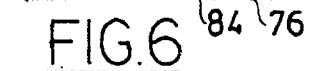
FIG. 6 is a partial, enlarged sectional view of the body warmer of FIG. 5.

In one preferred embodiment, illustrated in FIG. 6, the chamber 72 is formed by an outer layer of fabric 74, and outer layer of fabric 76, and disposed therebetween in chamber 72 an insulating laminated structure 78 comprised of insulating fibrous material 80 bonded to and disposed between sheets of fabric 82 and 84. In one embodiment, polyester fiberfill is the insulating fibrous material, and cotton fabric is used as fabrics 82 and 84.

In the embodiment illustrated in FIG. 6, the laminated structure 78 is from about 0.1 to about 0.4 inches, and the total thickness of the chamber 72 (including its outermost walls) is from about 0.3 to about 0.7 inches.

It is to be understood that the aforementioned description is illustrative only and that changes can be made in the apparatus, in the ingredients and their proportions, and in the sequence of combinations and process steps, as well as in other aspects of the invention discussed herein, without departing from the scope of the invention as defined in the following claims.

I claim:

1. A body warmer comprised of a fabric shell and an interior chamber, wherein said shell is comprised of a central body, a right flap joined to said central body, and a left flap joined to said central body, and wherein:
   (a) said shell is comprised of a front section and a back section joined to said front section, wherein said chamber is formed between said front section and said back section;
   (b) said central body of said shell is comprised of a top portion integrally connected to a bottom portion, wherein:
      1. said top portion has a substantially rectangular shape with a width of from about 6 to about 8 inches and a length of from about 23 to about 29 inches,
      2. said bottom portion is integrally joined to said top portion and has a length which decreases from its top to its bottom, wherein the bottom of said bottom portion has a length which is from about 70 to about 90 percent of the length of said top portion,
      3. the combined width of said top portion and said bottom portion is from about 1.5 to about 2.5 times as great as the width of said top portion, and
      4. at least about 80 volume percent of said chamber formed between said front section and said back section which is disposed in said central body of said shell is comprised of a laminated insulating structure comprised of a first fabric layer, an intermediate fibrous insulating layer joined to said first fabric layer, and a second fabric layer joined to said intermediate fibrous insulating layer; and (c) each of said right flap and said left flap is comprised of releasable attachment means and has a substantially rectangular shape, a width of from about 5 to about 8 inches, and a length of from about 8 to about 16 inches.

2. The body warmer as recited in claim 1, wherein said shell consists essentially of corduroy fabric.

3. The body warmer as recited in claim 2, wherein said corduroy fabric consists essentially of cotton.

4. The body warmer as recited in claim 3, wherein each of said right flap and said left flap has a length which is at least about 25 percent of said length of said top portion of said central body of said shell.

5. The body warmer as recited in claim 4, wherein said length of said right flap is substantially equal to said length of said left flap.

6. The body warmer as recited in claim 5, wherein the width of said left flap is substantially equal to the width of said right flap.

7. The body warmer as recited in claim 6, wherein the width of said left flap is substantially equal to the width of said top portion of said central body of said shell.

8. The body warmer as recited in claim 7, wherein said releasable attachment means comprises separable hook fasteners and loop fasteners.

9. The body warmer as recited in claim 8, wherein said separable hook fasteners and said separable loop fasteners consist essentially of fabric material.

10. The body warmer as recited in claim 9, wherein said central body of said shell has a width which is from about 1.6 to about 2.0 times as great as said width of said top portion of said central body.

11. The body warmer as recited in claim 10, wherein said intermediate fibrous insulating layer consists essentially of polyester fiberfill material.

12. The body warmer as recited in claim 11, wherein said first fabric layer consists essentially of cotton.

13. The body warmer as recited in claim 12, wherein said second fabric layer consists essentially of cotton.

14. The body warmer as recited in claim 13, wherein said laminated insulating structure is from about 0.1 to about 0.4 inches thick.

15. The body warmer as recited in claim 14, wherein said central body of said body warmer has a thickness of from about 0.3 to about 0.7 inches.

* * * * *